(12) United States Patent  
Xu et al.

(10) Patent No.: US 10,910,099 B2
(45) Date of Patent: Feb. 2, 2021

(54) SEGMENTATION, LANDMARK DETECTION AND VIEW CLASSIFICATION USING MULTI-TASK LEARNING

(71) Applicant: Siemens Healthcare GmbH, Erlangen (DE)

(72) Inventors: Zhoubing Xu, Plainsboro, NJ (US); Yuankai Huo, Nashville, TN (US); Jin-hyeong Park, Princeton, NJ (US); Sasa Grbic, Plainsboro, NJ (US); Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 95 days.

(21) Appl. No.: 16/272,169

(22) Filed: Feb. 11, 2019

(65) Prior Publication Data
US 2019/0259493 A1    Aug. 22, 2019

Related U.S. Application Data

(60) Provisional application No. 62/632,494, filed on Feb. 20, 2018.

(51) Int. Cl.
| | | |
|---|---|---|
| *G16H 30/40* | (2018.01) | |
| *G06T 7/00* | (2017.01) | |
| *G06T 7/11* | (2017.01) | |
| *G06K 9/62* | (2006.01) | |
| *G06K 9/34* | (2006.01) | |

(52) U.S. Cl.
CPC .............. *G16H 30/40* (2018.01); *G06K 9/34* (2013.01); *G06K 9/6267* (2013.01); *G06T 7/0012* (2013.01); *G06T 7/11* (2017.01); *G06K 2209/051* (2013.01);
(Continued)

(58) Field of Classification Search
CPC ........ G16H 30/40; G16H 50/70; G16H 50/20; G06K 9/34; G06K 9/6267; G06K 2209/051; G06T 7/0012; G06T 7/11; G06T 2207/10116; G06T 2207/20081; G06T 2207/10072; G06T 2207/30056; G06T 2207/30084
See application file for complete search history.

(56) References Cited

U.S. PATENT DOCUMENTS

| 10,506,984 B2 * | 12/2019 | Yu ............................. G06T 7/75 |
| 2007/0081712 A1 * | 4/2007 | Huang ...................... G06T 7/33 |
| | | 382/128 |

(Continued)

OTHER PUBLICATIONS

Hashimoto, Kazuma, et al. "A joint many-task model: Growing a neural network for multiple NLP tasks." arXiv preprint arXiv:1611.01587 (2016). pp. 1-15.

(Continued)

*Primary Examiner* — Aaron W Carter (57) ABSTRACT

Medical image data may be applied to a machine-learned network learned on training image data and associated image segmentations, landmarks, and view classifications to classify a view of the medical image data, detect a location of one or more landmarks in the medical image data, and segment a region in the medical image data based on the application of the medical image data to the machine-learned network. The classified view, the segmented region, or the location of the one or more landmarks may be output.

13 Claims, 6 Drawing Sheets

(52) U.S. Cl.
CPC ............... *G06T 2207/10072* (2013.01); *G06T 2207/10116* (2013.01); *G06T 2207/20081* (2013.01)

(56) References Cited

U.S. PATENT DOCUMENTS

| | | | | |
|---|---|---|---|---|
| 2010/0080434 | A1* | 4/2010 | Seifert | G06T 7/143 |
| | | | | 382/131 |
| 2011/0007954 | A1* | 1/2011 | Suehling | G06K 9/00362 |
| | | | | 382/128 |
| 2014/0093153 | A1* | 4/2014 | Sofka | G06T 7/0014 |
| | | | | 382/131 |
| 2014/0094679 | A1* | 4/2014 | Kovacs | G06T 7/136 |
| | | | | 600/407 |
| 2015/0238148 | A1* | 8/2015 | Georgescu | G06K 9/4628 |
| | | | | 600/408 |
| 2016/0063720 | A1* | 3/2016 | Han | G06T 7/10 |
| | | | | 382/131 |
| 2016/0328841 | A1* | 11/2016 | Lay | G06T 7/337 |
| 2016/0328855 | A1* | 11/2016 | Lay | G06K 9/4614 |
| 2017/0213339 | A1* | 7/2017 | Hibbard | G06K 9/6267 |
| 2017/0330319 | A1* | 11/2017 | Xu | G06T 7/73 |
| 2018/0211099 | A1* | 7/2018 | Ranjan | G06K 9/00281 |
| 2018/0225823 | A1* | 8/2018 | Zhou | G06N 3/0454 |
| 2019/0205606 | A1* | 7/2019 | Zhou | G06N 3/0445 |
| 2019/0251694 | A1* | 8/2019 | Han | G06T 7/174 |
| 2019/0259493 | A1* | 8/2019 | Xu | G16H 30/40 |
| 2019/0311478 | A1* | 10/2019 | Avendi | G06K 9/726 |
| 2019/0350564 | A1* | 11/2019 | Gajdos | G06T 5/00 |
| 2019/0354882 | A1* | 11/2019 | Sharma | G16H 30/40 |
| 2020/0051274 | A1* | 2/2020 | Siemionow | G06T 7/62 |
| 2020/0265579 | A1* | 8/2020 | Schmidt-Richberg | |
| | | | | G06K 9/6267 |

OTHER PUBLICATIONS

Kendall, Alex, Yarin Gal, and Roberto Cipolla. "Multi-Task Learning Using Uncertainty to Weigh Losses for Scene Geometry and Semantics." arXiv preprint arXiv:1705.07115 (2017). pp. 1-14.

Misra, Ishan, et al. "Cross-stitch networks for multi-task learning." Proceedings of the IEEE Conference on Computer Vision and Pattern Recognition. 2016. pp. 1-10.

Ranjan, Rajeev, et al. "Hyperface: A deep multi-task learning framework for face detection, landmark localization, pose estimation, and gender recognition." arXiv preprint arXiv:1603.01249 (2016). pp. 1-16.

Ruder, Sebastian, et al. "Sluice networks: Learning what to share between loosely related tasks." stat 1050 (2017): 23. pp. 1-10.

Ruder, Sebastian, et al. "Latent multi-task architecture learning." Proceedings of the AAAI Conference on Artificial Intelligence. vol. 33. 2019.

* cited by examiner

SEGMENTATION, LANDMARK DETECTION AND VIEW CLASSIFICATION USING MULTI-TASK LEARNING

PRIORITY CLAIM

This application claims priority to U.S. provisional application Ser. No. 62/632,494, filed 20 Feb. 2018, which is entirely incorporated by reference.

BACKGROUND

The present embodiments relate to segmentation, landmark detection, and view classification tasks for medical images. Segmentation may involve partitioning an image into parts. For example, an anatomic feature (such as a kidney or liver) may be segmented or partitioned from surrounding tissue. Landmark detection may involve determining a location of anatomical features in the image. View classification may involve labeling an image based on anatomy or other information present in the image. In some cases, the label may include a name of the anatomy along with an orientation (e.g. "transverse" or "longitudinal").

Imaging technicians may perform the segmentation, landmark detection, and view classification tasks manually. For example, the technician may manually input the identified view of an anatomic structure in a medical image, manually locate landmarks on the anatomical structure, and manually select the anatomy to segment from surrounding tissue. In some cases, computer programs may aid the technician in performing the segmentation, landmark detection, and/or view classification tasks on the medical images.

SUMMARY

By way of introduction, the preferred embodiments described below include methods, systems, instructions, and computer readable media for performing multiple diagnostic tasks on medical image data. A machine learning network may be trained based on medical image data and associated landmarks, segmentations, and view classifications to perform segmentation, landmark detection, and view classification on images. One network is trained to perform multiple functions or tasks. A landmark location, image segmentation, and view classification are generated based on applying medical image data to a trained machine-learned network.

In a first aspect, a method is provided for performing multiple diagnostic tasks on medical image data. First medical image data is received and applied to a machine learned network learned on second medical image data and associated image segmentations, landmarks, and view classifications. A view of the first medical image data is classified, a location of one or more landmarks in the first medical image data is detected, and a region in the first medical image data is segmented based on the application of the first medical image data to the machine-learned network. The classified view, the segmented region, or the location of the one or more landmarks are output.

In a second aspect, a method is provided for training a machine-learning network to perform multiple diagnostic tasks on medical image data. Medical image data and a plurality of landmark locations, a plurality of view classifications, and a plurality of image segmentations associated with the medical image data are stored. The machine-learning network is trained to segment anatomy, classify views, and detect landmarks based on the medical image data and the plurality of landmark locations, the plurality of view classifications, and the plurality of image segmentations.

In a third aspect, a medical imaging system for performing multiple diagnostic tasks on medical image data is provided. A memory stores a machine-learned network learned on second medical image data and ground truth including segmentation, landmark, and view classification for each of a plurality of second images of the second medical image data. An image processor configured to apply the medical image data to the machine-learned network and, based thereon, detect a location of one or more landmarks in the first medical image data, classify a view of the first medical image data, segment anatomy in the first medical image, or combinations thereof.

In connection with any of the aforementioned aspects (including, for instance, those set forth above in the Summary), the systems or methods may alternatively or additionally include any combination of one or more of the following aspects or features. The method for performing multiple diagnostic tasks on medical image data may include rescaling the first medical image data to match a resolution of the second medical image data. The method may include generating an anatomic label and an orientation of the first medical image data. In the method, detecting the location of the one or more landmarks may be based on the view classification. In the method, the first medical image data may be generated by an ultrasound, magnetic resonance tomography, or computed tomography imaging system. In the method, the second medical image data may be generated by an ultrasound, magnetic resonance tomography, or computed tomography imaging system, and the first medical image data may be generated by a different imaging modality than at least a portion of the second medical image data. In the method the processor may be part of a medical imaging system.

The method for training a machine-learning network to perform multiple diagnostic tasks on medical image data may include calculating a value of a loss function for the machine-learning network and updating the machine-learning network based on the value of the loss function. The method may include applying the medical image data to the machine-learning network, generating a probability heatmap of a location of one or more landmarks, segmentation regions, or landmarks and segmentation regions based on applying the medical image data to the machine-learning network, and determining a difference between the probability heatmap and the plurality of image segmentations, plurality of landmark locations, or plurality of image segmentations and plurality of landmark locations associated with the medical image data, where the value of the loss function may be based on the difference between the probability heatmap and the plurality of image segmentations, plurality of landmark locations, or plurality of image segmentations and plurality of landmark locations. The method may include identifying, by the processor, locations of two or more landmarks based on the heatmap, determining a first distance between the locations of the two or more landmarks, determining a second distance between two or more of the plurality of landmark locations associated with the medical image data and corresponding to the two or more landmarks, and determining a difference between the first distance and the second distance, where the value of the loss function may be based on the difference between the first distance and the second distance. The method may include determining a location of one or more landmarks based on the heatmap and determining a distance between the location of a first landmark of the one or more landmarks and a corresponding second landmark of the plurality of landmark locations associated with the medical image data, where the value of the loss function may be based on the distance between the first landmark and the corresponding second landmark. The method may include applying the heatmap and the plurality of image segmentations, plurality of landmark locations, or plurality of image segmentations and plurality of landmark locations associated with the medical image data to a general adversarial network, where the measure of similarity may be determined based on an output of the general adversarial network. In the method, the measure of similarity may be a measure of overlap between the segmentation region and at least one of the plurality of image segmentations associated with the medical image data. The method may include applying the medical image data to the machine-learning network to generate a first preliminary landmark location, calculating, by the processor, a first value of the loss function based on the first preliminary landmark location and the plurality of landmark locations associated with the medical image data, updating the machine-learning network based on the first value of the loss function, applying the medical image data to the machine-learning network to generate a first preliminary view classification and a second preliminary landmark location, calculating a second value of the loss function based on the first preliminary view classification, the plurality of view classifications associated with the medical image data, the second preliminary landmark location, and the plurality of landmark locations, updating the machine-learning network based on the second value of the loss function, applying the medical image data to the machine-learning network to generate a first preliminary segmentation, a second preliminary view classification, and a third preliminary landmark location, calculating a third value of the loss function based on the first preliminary segmentation, the plurality of image segmentations associated with the medical image data, the second preliminary view classification, the plurality of view classifications, the third preliminary landmark location, and the plurality of landmark locations, and updating the machine-learning network based on the third value of the loss function. In the method, the medical image data may include more than one type of anatomy.

The medical imaging system for performing multiple diagnostic tasks on medical image data may include an ultrasound, magnetic resonance tomography, or computed tomography medical imaging scanner configured to generate the first medical image data. In the system, the machine-learned network may have been trained on second medical image data having been generated by a further medical imaging scanner of a modality different from the medical imaging scanner configured to generate the first medical image data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Sonographers may manually perform landmark detection, view classification, and segmentation on ultrasound images. In some cases, computer programs may be used to aid the sonographer and decrease the time needed to perform each of these three tasks. Machine learning has been applied independently and individually to each task of landmark detection, view classification, and segmentation, resulting in multiple, individual machine-learning networks adapted for each task. However, using multiple networks to perform the tasks may be time consuming and resource intensive. Moreover, independent networks may not share information between tasks and may be adapted for only a single type of anatomy. In some cases, each independent network may be adapted to perform a single task on a single type of medical image and may not be generalizable to other medical imaging systems, anatomies, or tasks.

The embodiments described herein relate to a multi-purpose machine-learned network adapted to perform landmark detection, view classification, and segmentation. By applying one machine-learned network to all three tasks, resource consumption may be reduced. For example, less storage space may be used to store the multi-task machine-learned network than to store multiple, individual machine-learned networks for each task. In another example, the tasks may be performed simultaneously by the multi-task machine-learned network which may require fewer processing resources as compared to executing three independent machine-learned networks for each task simultaneously. In some cases, the machine-learned network may be able to perform all three tasks simultaneously on medical images in real time at a medical imaging workstation. Further, such a machine-learned network may be able to perform the three tasks on more than just ultrasound images. For example, the machine-learned network may be able to perform view classification, landmark detection, and segmentation on ultrasound, magnetic resonance, and/or computed tomography images. Additionally, the machine-learned network may be able to perform the tasks for multiple types of anatomy. Still further, the machine-learned network may be able to perform all three tasks and maintain accuracy in the tasks as compared to state-of-the-art independent, single-task networks. For example, a machine-learned network according to one or more of the enclosed embodiments achieved 90% accuracy on median Sorensen-Dice similarity coefficient for image segmentation, 89.5% classification accuracy over 11 classes of view classification, and the lowest distance error on landmark detection as compared to state-of-the-art independent networks. The accuracy of all tasks may be increased by including multiple tasks as compared to the accuracy for individual tasks.

Figure 1:
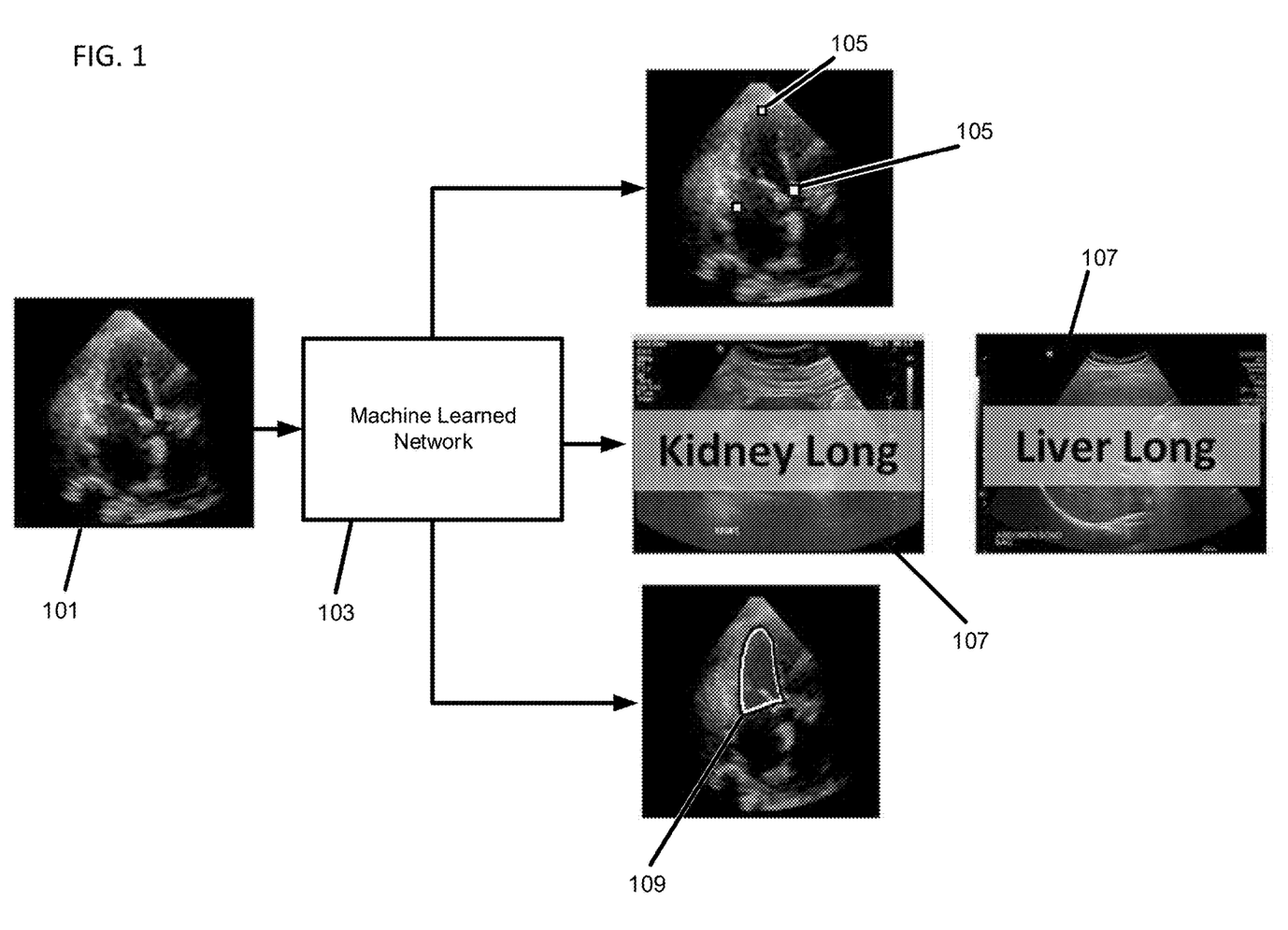
FIG. 1 illustrates one embodiment of a method for performing multiple diagnostic tasks on medical image data.

FIG. 1 illustrates one embodiment of a method for performing multiple diagnostic tasks 105-109 on image data 101. The medical image data 101 may be applied to a machine-learned network 103 to perform the tasks of detecting image landmarks 105, classifying views 107, and segmenting 109 the medical image data. All or less than all the tasks 105-109 may be performed. For example, the landmarks 105 may not be determined for certain view classifications where landmarks are unnecessary. Additional and/or different tasks may be performed. In some cases, the three tasks 105-109 may be performed simultaneously.

The image data 101 may be medical image data. The image data 101 may represent one or more anatomic structures. For example, the image data 101 may represent a liver, a kidney, and/or another organ. The image data may be generated by an ultrasound, magnetic resonance, computed tomography, or another imaging system.

The machine-learning network 103 may be a network that has been trained on image data to perform the three tasks of landmark detection 105, view classification 107, and segmentation 109. For example, the machine-learning network 103 may be a multi-task deep convolutional neural network (DCNN).

In some cases, the machine-learning network 103 may be trained on a training set of images captured with a first imaging system. For example, the training set of images may include images taken by an ultrasound imaging system. Once trained, the machine-learning network 103 may be able to perform the three tasks 105-109 on images 101 recorded by other imaging systems. For example, the trained machine-learning network 103 may be able to perform the tasks 105-109 on images 101 recorded by an ultrasound imaging system, but also images 101 recorded by a magnetic resonance or computed tomography imaging system. In this way, the machine-learning network 103 may be generalizable to perform the tasks 105-109 on images 101 recorded by multiple imaging systems. The machine-learning network 103 may be the machine learning network 303 of FIG. 3 and may be stored in the memory 605 of FIG. 6.

One or more landmarks 105 may be located within the image 101. The landmarks may be placed at the location of certain anatomic structures within the image. For example, landmarks 105 may be located at the position of ligaments or the porta hepatis in image data 101 representing a liver. The landmarks are located as points or regions in one, two, or three dimensions.

A view classification 107 may be determined for each image 101. In some cases, the view classification 107 may include a tag or name of the anatomy (e.g. kidney, spleen, liver). Additionally or alternatively, the view classification 107 may include an orientation of the anatomy (e.g. longitudinal, latitudinal) in the image 101. The machine-learned network may be able to classify multiple pieces of anatomy. Where multiple pieces of anatomy are present in the input image 101 or multiple labels apply to a given image, multiple view classifications may be determined.

The segmentation 109 may indicate a boundary between anatomy present in the image 101 and surrounding tissue. In some cases, the segmentation 109 may be a boundary of the anatomy identified in the view classification 107 and/or located landmarks. Additionally or alternatively, segmentation 107 may involve extracting, partitioning, or removing the segmented anatomy from the other information in the image 101. The segmentation labels the data as being a member or not of the segment, defines locations of a fit boundary, defines locations of the segment, or separates the data for the segment.

Figure 2:
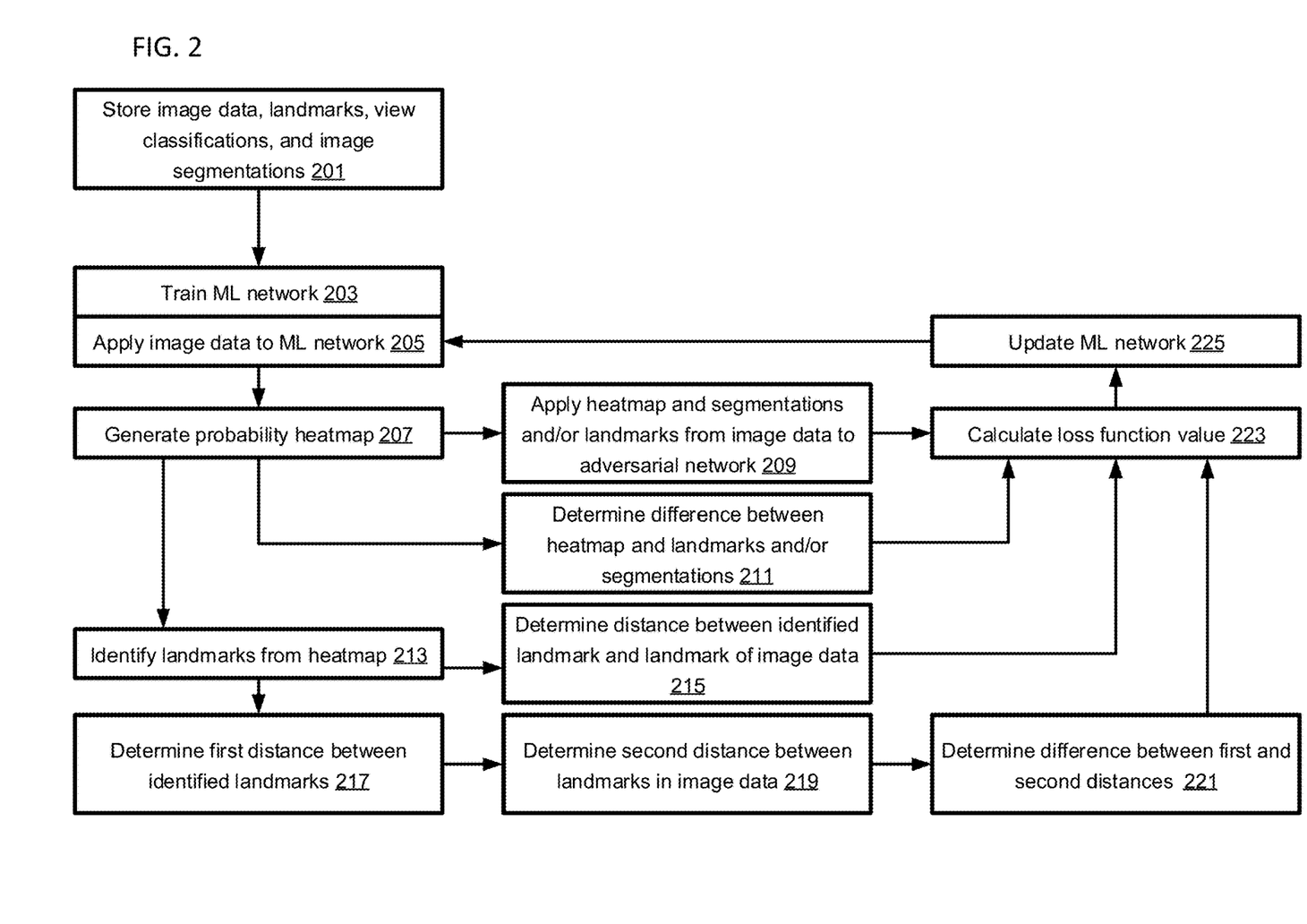
FIG. 2 is a flow chart diagram of an embodiment of a method for training a machine-learning network to perform multiple diagnostic tasks on medical image data.

FIG. 2 is a flow chart diagram of an embodiment of a method for training a machine-learning network to perform multiple diagnostic tasks on medical image data. More, fewer, or different acts may be performed. For example, acts 217, 219, or 221 may be omitted. In another example, acts 205, 223, and 225 are iterative and may be repeated.

The acts are performed in the order shown (e.g., numerical) but may be performed in any order. For example, act 211 may follow from act 213.

In act 201, training data is stored. The training data includes medical image data as samples with associated ground truths including the tasks to learn—landmark locations, view classifications, and image segmentations. In some cases, the medical image data is recorded by an ultrasound, magnetic resonance, or computed tomography imaging system. Other imaging systems may also record the medical image data. The medical image data contains multiple medical images, with each image having associated landmark locations, segmentations, and view classifications. The medical image data may include multiple, different, or multiple and different kinds of anatomy. For example, the medical image data may include one or more images of a liver and one or more images of a kidney. In this way, the machine-learning network may be generalized through training with the medical image data to perform the diagnostic tasks on images of multiple kinds of anatomy.

In act 203, the machine-learning network is trained to segment anatomy, classify views, and detect landmarks based on the medical image data. During training, the medical image data may be applied in act 205 to the machine-learning network to generate an intermediate landmark location, segmentation, and view classification. In some cases, the landmark locations, segmentations, and view classifications associated with the medical image data may be present in the image and require removal (e.g. by masking) prior to the medical image data being applied to the machine-learning network.

Based on comparisons between the intermediate landmark location, segmentation, and view classification generated by the machine-learning network and the landmark locations, segmentations, and view classifications associated with the medical image data, the machine-learning network may be updated. Acts 207-221 describe a method for comparing the intermediate landmark location, segmentation, and view classification generated by the machine-learning network and the landmark locations, segmentations, and view classifications associated with the medical image data in various ways, computing a loss function based on one or more of the comparisons, and updating the machine-learning network based on the loss function.

In act 207, a probability heatmap is generated. By applying the medical image data to the machine-learning network, the network may generate the heatmap. The probability heatmap may indicate a probability of a landmark or segmented region at a point in the medical image. For example, pixels in the medical image applied to the machine-learning network may be assigned a probability that the pixel (or the position represented by or occupied by the pixel) belongs to the anatomy to be segmented or to a landmark of the anatomy. The probability heatmap may be a probability heatmap 403a of FIG. 4.

In act 209, the heatmap and ground truth (segmentations, landmarks, and landmarks or segmentations associated with the medical image data) are applied to an adversarial network. The machine learning network together with the adversarial network may form a generative adversarial network (GAN). Applying the output of the machine-learning network to the adversarial network may help the landmarks and segmentations generated by the network (as indicated in the probability heatmap) more closely resemble the shape and position of the landmarks and segmentations associated with the medical image data. In some cases, the heatmap, landmarks, and segmentations are broken into patches before being applied to the adversarial network. Additionally or alternatively, the heatmap and segmentations, landmarks, and landmarks or segmentations associated with the medical image data are applied to the adversarial network using a Pix2Pix technique. For example, the outlines of the most probable regions in the heatmap for landmarks and segmentations may be compared to the landmarks and segmentations associated with the medical image data. In some cases, the adversarial network is updated based on an output of the adversarial network. The output may be a measure of similarity between the heatmap and ground truth (segmentations, landmarks, and landmarks or segmentations associated with the medical image data). The output may be the contribution 411 to the loss function of FIG. 4.

In act 211, a difference between the heatmap and segmentations, landmarks, or landmarks and segmentations associated with the medical image data may be determined. In some cases, the difference is based on a distance between corresponding pixels of the heatmap and the associated segmentations and landmarks. For example, the difference may be a least squared error or L2 loss between the heatmap and the associated segmentations and landmarks. Additionally or alternatively, the difference may be a measure of similarity or overlap between the heatmap and segmentations associated with the medical image data. For example, the difference may be a Sorensen-Dice similarity coefficient of the heatmap and segmentations associated with the medical image data. The difference may form part of a loss function. For example, the difference may be the loss calculation 403 of FIG. 4.

In act 213, landmarks may be identified from the heatmap. The position of the one or more landmarks may be identified as a most likely or most probable position of the landmark as indicated by the heatmap. Where there are multiple most likely positions in the heatmap, the position of the one or more landmarks may be based on the multiple most likely positions. For example, the position of the one or more landmarks may be determined as an average, center, or other combination of the multiple most likely positions in the heatmap.

In act 215, a distance between a landmark identified from the heatmap and a landmark associated with the medical image data may be determined. For example, a landmark associated with a piece of anatomy may be identified from the heatmap. The identified landmark may be compared to the landmark corresponding to the same piece of anatomy that is associated with the medical image data. A distance between the location of the identified landmark from the heatmap and the location of the corresponding landmark associated with the medical image data may be determined. A small or zero distance between the landmarks of the heatmap and the medical image data means that the landmark predicted by the machine-learning network is accurate. The distance between the landmarks may be used to determine a value of the loss function for the machine-learning network.

In act 217, a distance between a first landmark identified from the heatmap and a second landmark identified from the heatmap is determined. The first landmark may be associated with to a different anatomical structure than the second landmark. Where there are more than two landmarks identified from the heatmap, distances between each of the identified landmarks may be determined. For example, where there are three landmarks identified from the heatmap, up to three distances may be determined. As another example, where there are four landmarks, up to six distances may be determined. The landmarks may be the landmarks 105 of FIG. 1 or the landmarks 405a of FIG. 4.

In act 219, a distance between two or more landmarks associated with the medical image data may be determined. In some cases, the distances may be predetermined and stored prior to or during training of the machine-learning network. The predetermined or stored distance may be retrieved during act 219. The distance may be one of the distances between the ground truth landmarks 405b of FIG. 4.

In act 221, a difference between the distances between landmarks may be determined. For example, a distance between positions of a first and second landmark identified from the probability heatmap may be subtracted from a distance between positions of corresponding landmarks associated with the medical image data. In some cases, the difference may be an absolute value or squared. For multiple differences between pairs of distances, the differences may be added or averaged. The difference may form an input to the value of the loss function calculated in act 223. In some cases, the loss function may be calculated based on the sum of the squared differences.

In act 223, a value of the loss function may be calculated. The value of the loss function may be based on or be a function of one or more of the acts 209, 211, 215, and 221. For example, the value of the loss function may be determined to be a sum or weighted sum of one or more of the outcomes of the comparisons in acts 209, 211, 215, and 221. Additionally or alternatively, the value of the loss function may be based on comparing a view classification determined by the machine-learning network to a view classification associated with the medical image data. Training the machine-learning network may seek to optimize the loss function. For example, the value of the loss function may be reduced or minimized as the machine-learning network is trained. The loss function may be determined using the sum 317 of FIG. 3 or the sum 401 of FIG. 4.

In act 225, the machine-learning network is updated based on the value of the loss function. The loss function may reinforce behavior of the machine-learning network. All or less than all of the machine-learning network may be updated. For example, certain levels of the machine-learning network may be held constant while other levels of the machine-learning network are updated based on the loss function. In some cases, the machine-learning network may be updated when the value of the loss function exceeds a threshold value. For example, if the value of the loss function exceeds a threshold value, the machine-learning network is updated and another iteration of training is started (e.g. at act 205), whereas if the value of the loss function is below the threshold the training may be stopped. The training may be repeated over multiple samples of the medical imaging data.

The machine-learning network may be trained successively to perform each task. In some cases, the machine-learning network may be trained and updated to minimize a loss function for a first task, and then later trained for other tasks. Certain features, components, or layers of the machine-learning network may be held constant and not updated as the machine-learning network is successively trained for the tasks. For example, in a first iteration of training the machine-learning network, the medical image data may be applied to the machine-learning network to generate a preliminary landmark location and a first value of loss function determined based on the preliminary landmark location and the ground truth. The machine-learning network may be updated based on the first value of the loss function. In a second or later iteration of training, the medical image data may be applied to the machine-learning network to generate a preliminary landmark location and a preliminary view classification, and a second value of the loss function determined based on the preliminary landmark location, the preliminary view classification, and the ground truth. The machine-learning network may be updated based on the second value of the loss function. In a third or later iteration of training, the medical image data may be applied to the machine-learning network to generate a preliminary landmark location, a preliminary view classification, and a preliminary segmentation, and a third value of the loss function determined based on the preliminary landmark location, the preliminary view classification, the preliminary segmentation and the ground truth. The machine-learning network may be updated based on the third value of the loss function. Alternatively, the machine-learning network may be updated using a combination loss function where the training and corresponding updates are for all tasks at once.

After one or more iterations of calculating the loss function and updating the machine-learning network, the network may exit training and be stored for use. After training, the network may be referred to as a machine-learned network.

Figure 3:
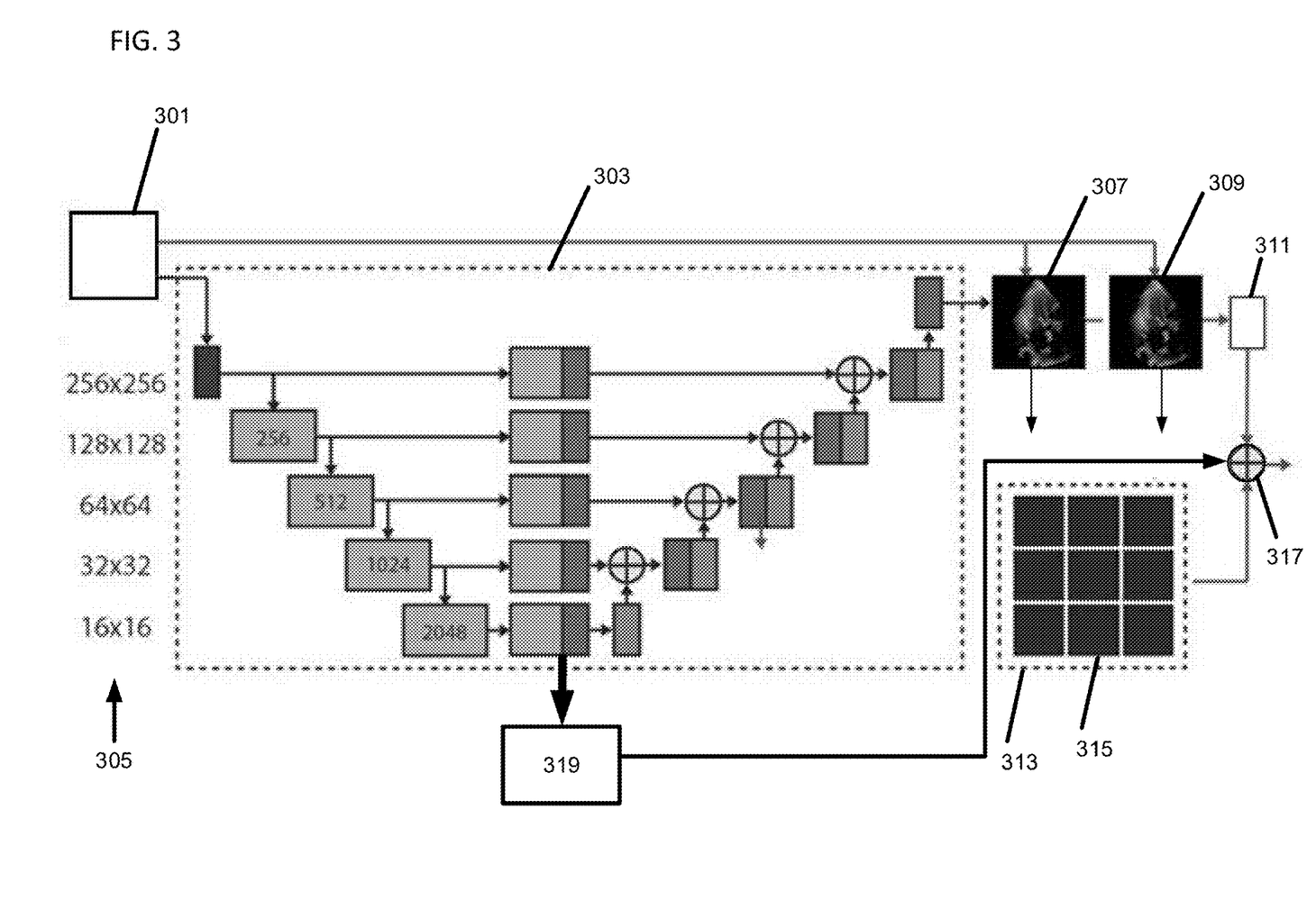
FIG. 3 is a schematic of an example structure or architecture of a machine-learning network for performing multiple diagnostic tasks on medical image data 301.

FIG. 3 is a schematic of a structure of a machine-learning network for learning to perform multiple diagnostic tasks on medical image data 301. The medical image data may be input to the machine-learning network 303 containing multiple levels 305. The machine-learning network may be a generative network, such as a U-net or image-to-image network. An output segmentation 307 may be generated by the network 303 and compared to a ground truth segmentation 309 to determine a loss 311. The output segmentation 307 and ground truth segmentation 309 may be applied to an adversarial network 313 where patches 315 are compared. The loss 311 and the output of the adversarial network 313 may be summed 317 to determine a total loss function. A view classification 319 may be generated by the network 303.

The medical image data 301 may be image data generated by a medical imaging system such as ultrasound, magnetic resonance, or computed tomography. The medical image data 301 may be the medical image data 101 of FIG. 1. The medical image data 301 may be rescaled prior to being applied to the machine-learning network 303. In some cases, the medical image data 301 may be rescaled to match dimensions of other image data used to train the machine-learning network 303. For example, all medical image data may be rescaled to dimensions of 512 pixels by 512 pixels. In some cases, the medical image data may not need to be rescaled.

The machine-learning network 303 may be a deep learning network or other type of network. The machine-learning network 303 may be the machine-learning network 103 of FIG. 1. The machine-learning network 303 may be trained with image data to perform the diagnostic tasks of segmentation, landmark detection, and view classification.

The levels 305 may be different components of the machine-learning network 303. The dimensions on the left of the machine-learning network describe the size of intermediate feature maps from the medical image data in pixels present at each level. The design of the input dimensions for 303 is flexible to be able to compatible with different applications. In some cases, the medical image data 301 may be applied first to a convolutional layer of the machine-learning network 303. Subsequent levels 305 of the machine-learning network may include convolutional layers, residual blocks, global convolutional networks, boundary refinement layers, deconvolutional layers, or other layers. In a multi-task framework, each of the different tasks (e.g. segmentation, view classification, and landmark identification) are able to share levels 305 and other features of the machine-learning network 303.

The output segmentation 307 may be generated by the machine-learning network 303. The output segmentation 307 may indicate a boundary of all or part of a piece of anatomy. The boundary may separate or partition the segmented anatomy from surrounding tissue. The segmentation 307 may be the segmentation 109 of FIG. 1.

The ground truth segmentation 309 may be a segmentation associated with image data used to train the machine-learning network. When the machine-learning network 303 is being trained, the ground truth segmentation 309 may be associated with the input image 301.

The loss 311 may be determined based on the generated segmentation 307 and a ground truth segmentation 309. The loss 311 may be determined according to act 223 of FIG. 2 or element 401 of FIG. 4. In some cases, the loss includes or is calculated based on a difference between the output segmentation 307 and the ground truth segmentation 309. For example, the difference may be determined according to act 211 of FIG. 2. The loss may be a Sorensen-Dice coefficient determined based on a similarity or overlap between the output segmentation 307 and the ground truth segmentation 309.

The adversarial network 313 may accept as inputs the output segmentation 307 from the machine-learning network 303 and the ground truth segmentation 309 associated with the input medical image data 301. The machine-learning network 303 may form a generative adversarial network together with the adversarial network 313. The adversarial network 313 may provide an output value or a loss value based on how closely the output segmentation 307 resembles the ground truth segmentation 309. For example, a discriminator of the adversarial network 313 may generate an error rate based on the output segmentation 307 and the ground truth segmentation 309. The output segmentation 307 and the ground truth segmentation 309 may be broken into patches 315. The adversarial network 313 may determine the output or loss for each patch 315.

The sum 317 may combine or include one or more sources of error for backpropagation to the machine-learning network 303. For example, the sum may add the loss 311 to the output of the adversarial network 313. The sum 317 may also include other sources of error or loss. Additional comparisons between the ground truth and view classification 319, segmentation 307, and landmarks generated by the machine learning network 303 may be summed. For example, the sources of error as determined in acts 209, 211, 215, and 221 of FIG. 2 may be added together in the sum 317. In another example, the loss includes a comparison of the view classification 319 generated by the machine-learning network 303 to a ground truth view classification associated with the medical image data 301. The sum 317 may be the sum 401 of FIG. 4.

The view classification 319 may be generated by the machine-learning network 303. For example, features for generating the view classification 319 may be extracted by applying global average pooling to the output of an encoder of the machine-learning network 303. The view classification 319 may include a name or type of one or more anatomic structures present in the medical image data 301. The view classification may be checked against a ground truth view classification associated with the medical image data 301. The result of the check may be part of the sum 317. The view classification 319 may be the view classification 107 of FIG. 1.

Figure 4:
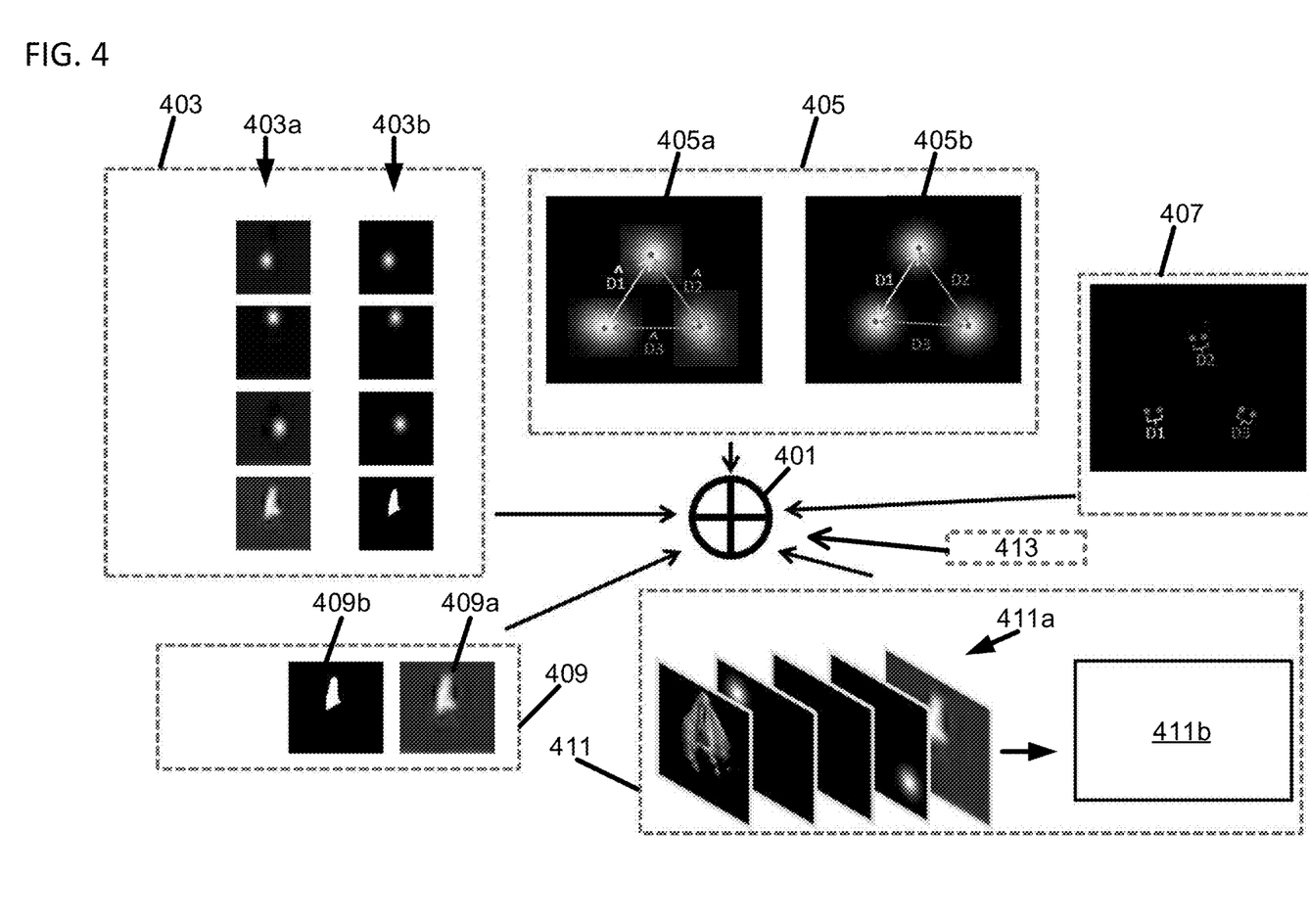
FIG. 4 is a schematic representation of a loss function for training a machine-learning network, according to one embodiment.

FIG. 4 is a schematic representation of a loss function for training a machine-learning network. A value of the loss function may be determined by a sum 401 or other combination of multiple loss contributions 403, 405, 407, 409, 411, and 413. The sum 401 may be the sum 317 of FIG. 3.

A first loss contribution 403 may be a comparison of landmarks and segments 403a generated by a machine-learning network to corresponding landmarks and segments 403b associated with medical image data applied to the machine-learning network. A value of the first loss contribution 403 may be determined according to act 211 of FIG. 2.

A second loss contribution 405 may be a comparison of distances between different landmarks 405a generated by the machine-learning network and the same different landmarks 405b associated with the medical image data (i.e., ground truth). Distances $\bar{D1}$, $\bar{D2}$, and $\bar{D3}$ may be determined between the landmarks 405a located by the machine-learning network. Distances D1, D2, and D3 may be determined between the landmarks 405b associated with the medical image data. The corresponding distances may then be compared. For example, $\bar{D1}$ may be subtracted from D1, $\bar{D2}$ may be subtracted from D2, and $\bar{D3}$ may be subtracted from D3. The differences may be squared or have their absolute value taken so that the differences are all positive numbers. The differences may then be summed or averaged to determine a value of the second loss contribution 405. The second loss contribution 405 may be determined as detailed in act 221 of FIG. 2. Though the second loss contribution 405 as illustrated shows three landmarks and three distances, more or fewer landmarks or distances may be determined.

A third loss contribution 407 may be a sum of distances between the same landmarks in the network output and the ground truth. The two landmarks may correspond to a location of the same anatomic structure in the medical image data. A distance (e.g., D1) may be determined between a landmark generated by the machine-learning network (e.g. one of the landmarks from 405a) and a ground truth landmark associated with the medical image data (e.g. a corresponding landmark from 405b). The landmark generated by the machine-learning network may be determined based on a probability heatmap of possible locations of the landmark. The distance between each generated landmark and ground truth landmark may be determined and summed. For example, the distance between the landmarks may be determined as in act 215 of FIG. 2. Though the third loss contribution 407 as illustrated shows three pairs of landmarks, more or fewer pairs may be determined.

A fourth loss contribution 409 may be a measure of similarity or overlap between a segmentation generated by the machine-learning network 409a and a segmentation 409b associated with the medical image data. For example, the fourth loss contribution may be determined as detailed in act 211 of FIG. 2 or element 311 of FIG. 3. In some cases, the measure of similarity may be a Sorensen-Dice coefficient.

A fifth loss contribution 411 may be determined by applying multiple segmentations and landmarks 411a to an adversarial network 411b. The adversarial network 411b may be the adversarial network 313 of FIG. 3. In some cases, the landmark and segmentation heatmap and the segmentations and landmarks associated with the medical image data may be applied to the adversarial network 411b. The adversarial network may output a loss value or coefficient based on how closely the two types of input (e.g. landmarks or segmentations generated by the machine-learning network and ground truth associated with the medical image data) resemble one another. The value or loss of the adversarial network 411b may be determined on a patch-by-patch basis for the segmentations and landmarks (or the heatmap) determined by the machine-learning network and segmentations and landmarks associated with the medical image data. The fifth loss contribution 411 may be determined of act 209 of FIG. 2.

A sixth loss contribution 413 may be determined by comparing a view classification generated by the machine-learning classifier to the ground truth view classification associated with the medical image data. In some cases, where the view classification determined by the machine-learning network matches the ground truth classification, the comparison may return a value of zero. Where the determined view classification does not match the ground truth, the comparison may return a non-zero value.

Figure 5:
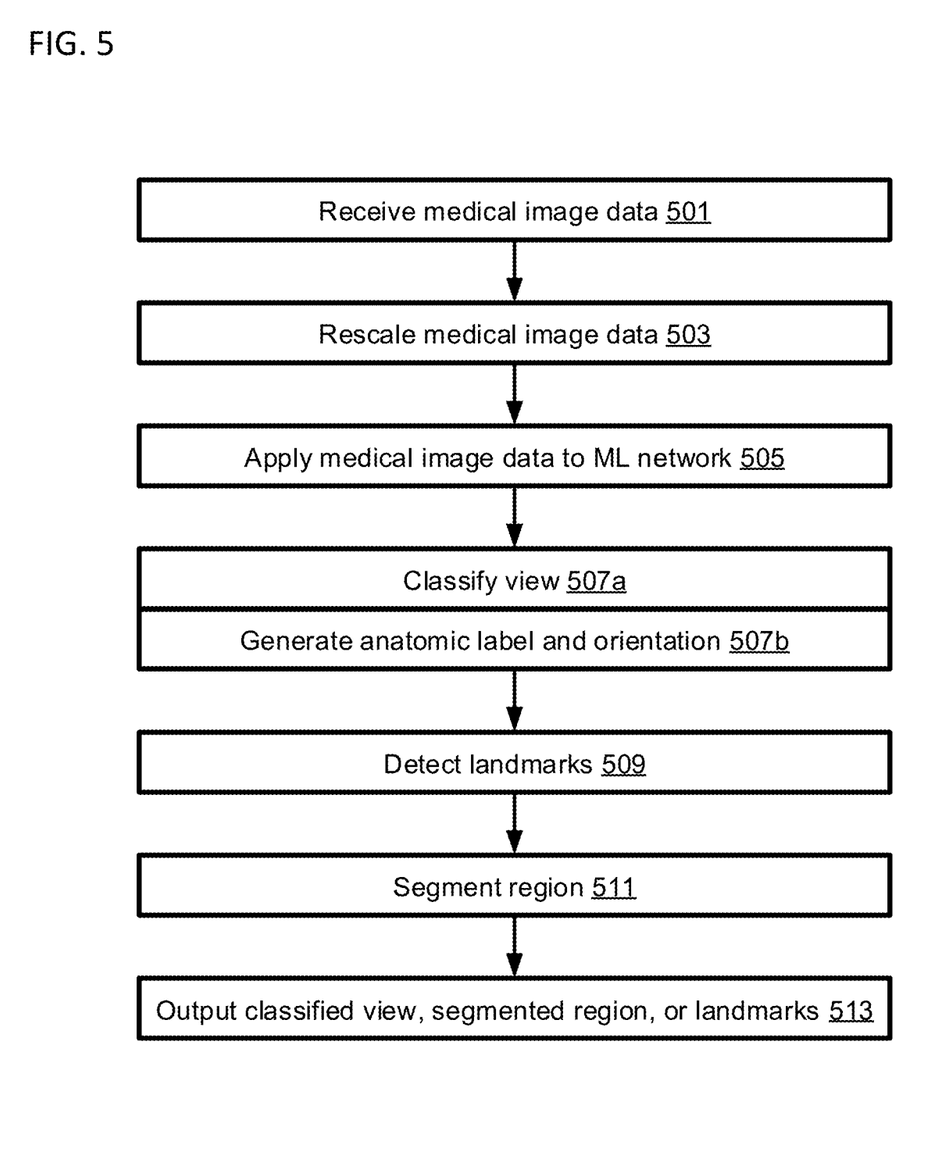
FIG. 5 is a flow chart diagram of one embodiment of a method for performing multiple diagnostic tasks on medical image data with one machine-learned network.

FIG. 5 is a flow chart diagram of one embodiment of a method for performing multiple diagnostic tasks on medical image data using one machine-learned network. More, fewer, or different tasks may be performed. For example, acts 513, 511, or 509 may be omitted.

The acts may be performed by an image processor. For example, the processor 603 of the medical imaging system 601 of FIG. 6 may be configured to perform the acts. Instructions to cause the processor to perform the acts when executed may be stored in the memory 605 of FIG. 6.

The acts may be performed in the order shown (e.g., top to bottom or numerical) but may be performed in any order. For example, act 507a may follow from act 511. In some cases, acts 507, 509, and 511 may be performed simultaneously. As another example, acts 507, 509, 511, and 513 occur simultaneously in response to act 505.

In act 501, medical image data may be received. The medical image data may be data that was not used to train the machine-learning network. In some cases, the medical image data may be referred to as "unseen data" where the data has not previously been applied to the machine-learning network. The medical image data may be recorded by medical imaging system. For example, the medical image data may be acquired by a scan of a patient by an ultrasound, magnetic resonance, or computed tomography imaging system. The machine-learning network may have been trained or configured to perform diagnostic tasks on medical images recorded by one or more types of medical imaging systems. The medical image data may be the image data 101 of FIG. 1 or, in some cases, the image data 301 of FIG. 3.

In act 503, The medical image data may be resized or rescaled to a different size or resolution. In some cases, the medical imaging data may be rescaled or resized to match the size or resolution of the image data used to train the machine-learning network. For example, where the machine-learning network was trained on image data having a resolution of 512 pixels by 512 pixels, the medical image data may be rescaled to match the resolution. The rescaling or resizing may be a form of preprocessing performed on the medical image data prior to the medical image data being applied to the machine-learning network in act 503.

In act 505, the medical image data may be applied to a trained or machine-learned network. The machine-learning network may be learned on a training set of medical images and associated view classifications, landmark locations, and segmentations. In some cases, the medical image data applied to the machine-learned network may be recorded by a different medical imaging system than the training medical image data. For example, the training medical image data may be recorded by an ultrasound imaging system and the medical imaging data applied to the machine-learned network may be recorded by a computed tomography or magnetic resonance imaging modality. The machine-learned network may be trained to perform view classification, landmark detection, and image segmentation on an image applied to the network. The machine-learned network may be the network 103 of FIG. 1.

In act 507*a*, a view of the medical image data may be classified. By applying the medical image data to the machine-learning network, the network outputs a classification. The view classification may be the view classification 107 of FIG. 1.

In act 507*b*, an anatomic label and an orientation of anatomy represented in the medical image data may be generated for the classification of act 505*a*. The anatomic label may be a name or type of the anatomy. For example, the label may be "kidney," "right kidney," or "left kidney." The orientation may be an orientation of the anatomy in reference to a viewing point or to a side of the body. For example, the orientation may indicate a longitudinal or latitudinal view. In some cases, there may be multiple pieces of anatomy represented in the medical image data. The view of each piece of anatomy may be classified.

In act 509, a location of one or more landmarks in the medical image data may be detected. By applying the medical image data to the machine-learning network, the network outputs a location of one or more landmarks. In some cases, the detection of the landmarks may be based on the view classification. For example, where a view is classified as having a latitudinal view of a kidney, the location of kidney landmarks visible from the latitudinal view may be detected. In some other cases, the view classification will identify a piece of anatomy that does not have landmarks or for which landmark measurements are unnecessary or not useful. In these cases, the landmarks may not be detected. The landmark may be the landmark 105 of FIG. 1.

In act 511, a region of the medical image data may be segmented. By applying the medical image data to the machine-learned network, the network outputs a segmentation region of the medical image data. The segmentation region may correspond to a boundary of the classified anatomy. In some cases, the segmentation may extract, partition or remove the anatomy from surrounding tissue represented in the medical image data. The segmentation may be the segmentation 109 of FIG. 1.

In act 513, the classified view, the segmented region, or the location of the one or more landmarks may be output. For example, the view, segmentation, and landmarks may be output to a display of a medical imaging system, such as the display 609 of FIG. 6. In some cases, the output may include the segmented region, or the location of the one or more landmarks in conjunction with the medical image data. For example, the segmented region, or the location of the one or more landmarks may be overlaid on the medical image data. The segmented region, or the location of the one or more landmarks may each be layers together in a composite image with the medical image data or each of the segmented region, or the location of the one or more landmarks may be presented in the output in a separate composite image with the medical image data. In some cases, the segmentation, view classification, and landmark detection may be performed and output in real time as the medical imaging system acquires medical image data. The output may be used by an imaging technician or other user to make a diagnosis of the anatomy represented in the medical image data.

Figure 6:
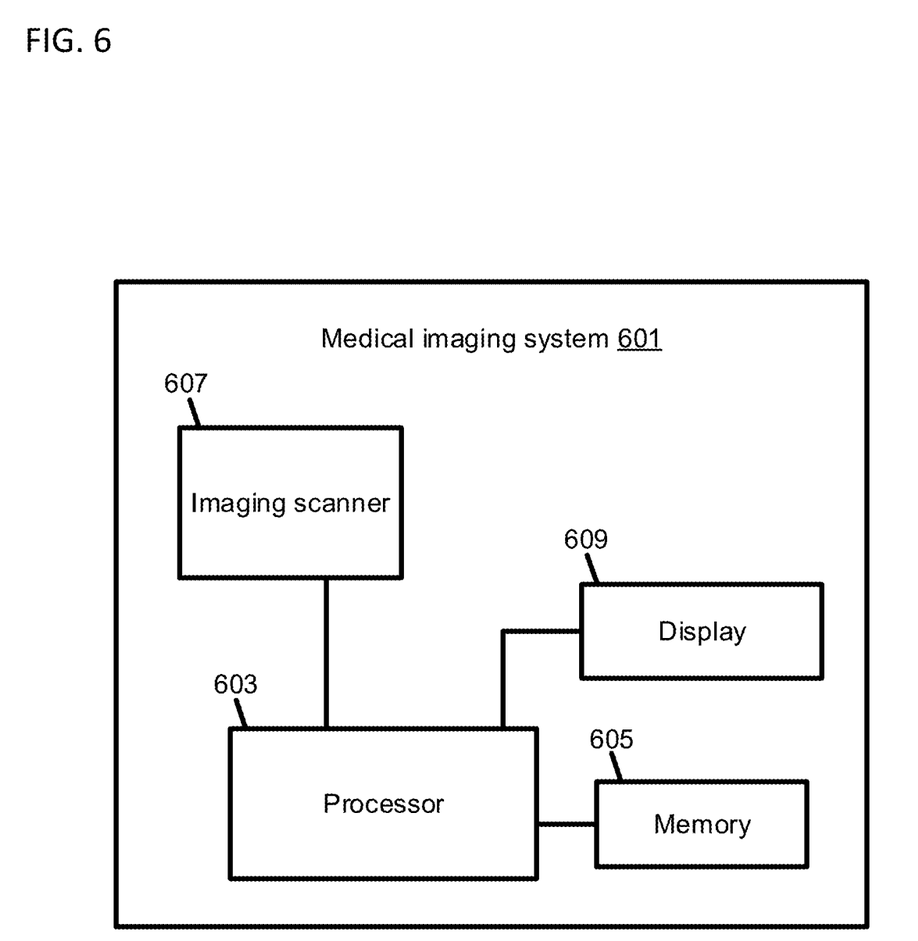
FIG. 6 is a block diagram of one embodiment of a medical imaging system for performing multiple diagnostic tasks on medical image data.

FIG. 6 is a block diagram of a medical imaging system 601 for performing multiple diagnostic tasks on medical image data. The medical imaging system 601 may include a processor 603 coupled with a memory 605 and in communication with an imaging scanner 607 and a display 609. The medical imaging system 601 performs the acts of FIG. 5 or other acts.

The processor 601 may be a general purpose or application specific processor. In some cases, the processor 601 may be an image processor suitable for performing tasks on image data. The processor 601 may be configured to apply the medical image data to a machine-learned network stored in the memory 605. Based on applying the medical image data to the machine-learned network, the processor 601 may be configured to perform one or more of: detect a location of one or more landmarks in the first medical image data, classify a view of the first medical image data, and segment anatomy in the first medical image.

The memory 605 may be a non-transitory computer readable storage medium. The memory 605 may be configured to store instructions that cause the processor to perform an operation. For example, the memory 605 may store instructions that, when executed by the processor 601, cause the processor 601 to perform one or more acts of FIG. 2 or FIG. 5. The memory may be configured to store medical image data and a machine-learned network trained on ground truth medical image data and associated ground truth segmentations, landmarks, and view classifications. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The memory 605 may also be configured to store the training dataset, training deep network architecture, and the application deep network architecture.

The imaging scanner 607 may be a medical imaging scanner. For example, the imaging scanner 607 may be an ultrasound, magnetic resonance, or computed tomography imaging scanner. The imaging scanner may include an emitter and a receiver configured to generate the medical image data.

The display 609 may be configured to accept user input and to display audiovisual information to the user. In some cases, the display 609 may include a screen configured to present the audiovisual information. For example, the display 609 may present the medical image, output segmentation, view classification, and/or landmark location using the screen. The display 609 may include a user input device. In some cases, the user may input information relating to the diagnostic tasks to be performed on the medical imaging data with the user input device of the display 609. For example, the user may select one, two, or all three of the diagnostic tasks to be performed on the medical imaging data. In another example, one or more tasks are performed automatically without user selection.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for performing multiple diagnostic tasks on medical image data, the method comprising:
   receiving, by a processor, first medical image data;
   applying, by the processor, the first medical image data to a machine-learned network learned on second medical image data and associated image segmentations, landmarks, and view classifications;
   classifying, by the processor, a view of the first medical image data based on the application of the first medical image data to the machine-learned network;
   detecting, by the processor, a location of one or more landmarks in the first medical image data based on the application of the first medical image data to the machine-learned network;
   segmenting, by the processor, a region in the first medical image data based on the application of the first medical image data to the machine-learned network; and
   outputting, by the processor, the classified view, the segmented region, or the location of the one or more landmarks.

2. The method of claim 1, further comprising:
   rescaling, by a processor, the first medical image data to match a resolution of the second medical image data.

3. The method of claim 1, wherein classifying the view further comprises:
   generating an anatomic label and an orientation of the first medical image data.

4. The method of claim 1, wherein detecting the location of the one or more landmarks is based on the view classification.

5. The method of claim 1, wherein the first medical image data is generated by an ultrasound, magnetic resonance tomography, or computed tomography imaging system.

6. The method of claim 5, wherein the second medical image data is generated by an ultrasound, magnetic resonance tomography, or computed tomography imaging system, and wherein the first medical image data is generated by a different imaging modality than at least a portion of the second medical image data.

7. The method of claim 1, wherein the processor is part of a medical imaging system.

8. A medical imaging system for performing multiple diagnostic tasks on medical image data, the system comprising:
   a memory storing a machine-learned network learned on second medical image data and ground truth including segmentation, landmark, and view classification for each of a plurality of second images of the second medical image data; and
   an image processor configured to apply the medical image data to the machine-learned network and, based thereon, detect a location of one or more landmarks in the first medical image data, classify a view of the first medical image data, segment anatomy in the first medical image, or combinations thereof.

9. The system of claim 8, further comprising:
   an ultrasound, magnetic resonance tomography, or computed tomography medical imaging scanner configured to generate the first medical image data.

10. The system of claim 9, wherein the machine-learned network was trained on second medical image data having been generated by a further medical imaging scanner of a modality different from the medical imaging scanner configured to generate the first medical image data.

11. The method of claim 1, wherein the view of the first medical image data is an orientation of the first medical image data in reference to a viewing point or to a side of a body.

12. The method of claim 3, wherein the orientation of the first medical image data is referenced to a viewing point or to a side of a body.

13. The system of claim 8, wherein the view of the first medical image data is an orientation of the first medical image data in reference to a viewing point or to a side of a body.

* * * * *